US009388158B2

(12) United States Patent
Kikumoto et al.

(10) Patent No.: US 9,388,158 B2
(45) Date of Patent: Jul. 12, 2016

(54) PRODUCTION METHOD FOR CYCLOPENTANONE DERIVATIVE, INTERMEDIATE COMPOUND, AND PRODUCTION METHOD FOR INTERMEDIATE COMPOUND

(71) Applicant: Kureha Corporation, Tokyo (JP)

(72) Inventors: Shigeyuki Kikumoto, Tokyo (JP); Hisashi Kanno, Tokyo (JP)

(73) Assignee: KUREHA CORPORATION, Tokyo (JP)

(*) Notice: Subject to any disclaimer, the term of this patent is extended or adjusted under 35 U.S.C. 154(b) by 0 days.

(21) Appl. No.: 14/372,884

(22) PCT Filed: Dec. 10, 2012

(86) PCT No.: PCT/JP2012/081903
§ 371 (c)(1),
(2) Date: Jul. 17, 2014

(87) PCT Pub. No.: WO2013/108514
PCT Pub. Date: Jul. 25, 2013

(65) Prior Publication Data
US 2015/0025254 A1 Jan. 22, 2015

(30) Foreign Application Priority Data

Jan. 17, 2012 (JP) ................................. 2012-007522

(51) Int. Cl.
C07D 319/08 (2006.01)
C07C 45/65 (2006.01)
C07D 249/08 (2006.01)
C07C 45/75 (2006.01)
C07C 45/64 (2006.01)
C07C 49/493 (2006.01)
C07C 49/747 (2006.01)
C07C 45/67 (2006.01)

(52) U.S. Cl.
CPC .............. C07D 319/08 (2013.01); C07C 45/64 (2013.01); C07C 45/65 (2013.01); C07C 45/676 (2013.01); C07C 45/75 (2013.01); C07C 49/493 (2013.01); C07C 49/747 (2013.01); C07D 249/08 (2013.01); C07C 2101/08 (2013.01)

(58) Field of Classification Search
CPC .... C07C 45/676; C07C 45/75; C07C 49/747; C07C 49/697; C07C 2101/08; C07C 45/64; C07C 45/65; C07C 49/493; C07D 249/08; C07D 319/08
See application file for complete search history.

(56) References Cited

U.S. PATENT DOCUMENTS 3,649,678 A 3/1972 Fusco et al.
5,286,737 A 2/1994 Kato et al.

FOREIGN PATENT DOCUMENTS

JP     2006-016355 A      1/2006
WO    WO 2011/070771    *  6/2011
WO    WO/2011/070771 A1   6/2011

OTHER PUBLICATIONS

International Preliminary Report on Patentability and English translation of Written Opinion issued Jul. 31, 2014, in PCT International Application No. PCT/JP2012/081903.
International Search Report of PCT/JP2012/081903 dated Mar. 5, 2013.
Müller, Paul; Siegfried, Bernard; Decarboxylation of β-Ketoesters in Hexamethylphosphoric Triamide, Ferguson Press, Tetrahedron Letters, 1973, (37), 3565-8, Great Britain.
Henderson, Douglas; Richardson Kevan A.; Taylor, Richard J. K.; A Quick and Efficient Route to 2-Substituted Cyclopentanones and Cyclohexanones, School of Chemical Sciences, Synthesis, 1983, (12), 996-7, Norwich, United Kingdom.
Guerrab, Zineb; Schweiger, Stefan; Daou, Boujemäa; Ahmar, Mohammed; Cazes, Bernard; Lipase-catalyzed kinetic resolution of x-hydroxymethylcycloalkanones with a quaternary carbon center. Chemoenzymatic systhesis of chiral pseudoiridolactones, Tetrahedron:Assynmetry, 2010, 21(13-14), 1752-1757.

(Continued)

Primary Examiner — Valerie Rodriguez-Garcia
(74) Attorney, Agent, or Firm — Birch, Stewart, Kolasch & Birch, LLP

(57) ABSTRACT

The present invention is a production method for a compound represented by the following general formula (V), the method comprising a step of obtaining a compound represented by the following general formula (II) by reacting a compound represented by the following general formula (I) with an acid:

Chem. 1

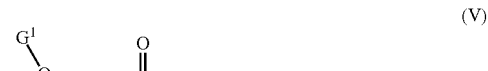

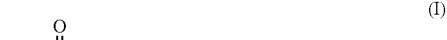

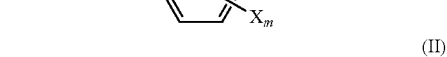

wherein, $G^1$ and $G^2$ are each a protecting group that dissociates under acidic conditions.

9 Claims, No Drawings

(56) References Cited

OTHER PUBLICATIONS

Chinese Office Action for Application No. 201280065774.1 dated Mar. 24, 2015 with English language translation.

Extended European Search Report, dated Jul. 20, 2015, for European Application No. 12866116.2.

Chinese Office Action for Application No. 201280065774.1 dated Sep. 6, 2015 with English language translation.

\* cited by examiner

PRODUCTION METHOD FOR CYCLOPENTANONE DERIVATIVE, INTERMEDIATE COMPOUND, AND PRODUCTION METHOD FOR INTERMEDIATE COMPOUND

TECHNICAL FIELD

The present invention relates to a novel production method for a cyclopentanone derivative, an intermediate compound of the cyclopentanone derivative, and a production method of the intermediate compound.

BACKGROUND ART

A certain type of 2-(halogenated hydrocarbon substituted)-5-benzyl-1-azolylmethylcyclopentanol derivative is described in Patent Document 1 as a compound that can be used as an active ingredient for agricultural and horticultural chemicals, industrial material protectants, and the like. A method for producing a 2-benzyl-5,5-bis(hydroxymethyl)-cyclopentanone derivative having a protected hydroxy group from a 1-benzyl-2-oxocyclopentane carboxylic acid alkyl ester derivative is also described in this document as a part of a step in the production method for this derivative.

CITATION LIST

Patent Literature

Patent Document 1: WO/2011/070771 (published Jun. 16, 2011)

SUMMARY OF INVENTION

Technical Problem

In order to mass-produce a 2-benzyl-5,5-bis(hydroxymethyl)-cyclopentanone derivative having a protected hydroxy group less expensively, it is necessary to improve the yield when producing a 2-benzyl-5,5-bis(hydroxymethyl)-cyclopentanone derivative having a protected hydroxy group from a 1-benzyl-2-oxocyclopentane carboxylic acid alkyl ester derivative.

The invention of the present application was conceived in light of the problem described above, and an object of the present invention is to provide a method for more efficiently producing a 2-benzyl-5,5-bis(hydroxymethyl)-cyclopentanone derivative having a protected hydroxy group, which is an intermediate compound of a compound that can be used as an active ingredient for agricultural and horticultural chemicals, industrial material protectants, and the like.

Solution to Problem

The present invention is a production method for a cyclopentanone derivative represented by general formula (V) below:

Chem. 1

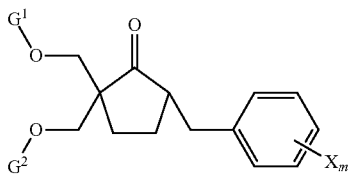

(V)

(in formula (V), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; $G^1$ and $G^2$ each represents a protecting group that dissociates under acidic conditions, $G^1$ and $G^2$ may be the same or different, and $G^1$ and $G^2$ may bond with one another to form a ring);

the method comprising a step of obtaining a compound represented by general formula (II) below by reacting a compound represented by general formula (I) below with an acid:

Chem. 2

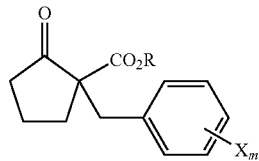

(I)

(in formula (I), X and m are each the same as X and m in formula (V), and R is an alkyl group having from 1 to 4 carbons);

Chem. 3

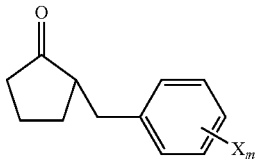

(II)

(in formula (II), X and m are each the same as X and m in formula (V)).

The present invention also provides a production method for a compound represented by general formula (II) above, wherein the compound represented by general formula (I) above is reacted with an acid.

The present invention also provides a production method for a compound represented by general formula (III) below:

Chem. 4

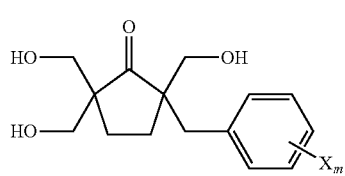

(III)

(in formula (III), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; and a plurality of X moieties may be the same or different when m is 2 or greater);

wherein a compound represented by general formula (II) above is obtained by reacting a compound represented by general formula (I) above with an acid, and this compound is further reacted with formaldehyde or a formaldehyde derivative.

The present invention also provides a production method for a compound represented by general formula (IV) below:

Chem. 5

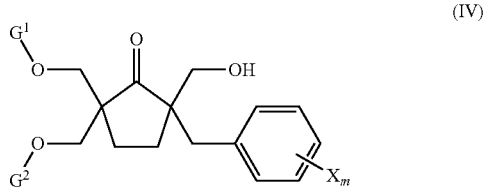

(IV)

(in formula (IV), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; $G^1$ and $G^2$ each represents a protecting group that dissociates under acidic conditions, $G^1$ and $G^2$ may be the same or different, and $G^1$ and $G^2$ may bond with one another to form a ring);
wherein a compound represented by general formula (II) above is obtained by reacting a compound represented by general formula (I) above with an acid; a compound represented by general formula (III) above is obtained by further reacting this compound with formaldehyde or a formaldehyde derivative; and some of the hydroxy groups of this compound are further protected by protecting groups that dissociate under acidic conditions.

The present invention further provides a production method for a compound represented by general formula (III) above, wherein a compound represented by general formula (II) above is reacted with formaldehyde or a formaldehyde derivative.

The present invention further provides a production method for a compound represented by the general formula (IV), wherein some of the hydroxy groups of a compound represented by general formula (III) above are protected by protecting groups that dissociate under acidic conditions.

The present invention further provides a production method for a compound represented by general formula (V) above, wherein a compound represented by the general formula (IV) is dehydroxymethylated under basic conditions.

The present invention further includes an intermediate compound in the production of a cyclopentanone derivative represented by general formula (V) above, the intermediate compound being represented by general formula (III) above.

The present invention further includes an intermediate compound in the production of a cyclopentanone derivative represented by general formula (V) above, the intermediate compound being represented by general formula (IV) above.

Advantageous Effects of Invention

With the present invention, it is possible to more efficiently produce a 2-benzyl-5,5-bis(hydroxymethyl)-cyclopentanone derivative having a protected hydroxy group.

DESCRIPTION OF EMBODIMENTS

An embodiment of the production method for a cyclopentanone derivative according to the present invention will be described hereinafter.

The production method for a cyclopentanone derivative according to the present invention is a production method for a cyclopentanone derivative represented by the following general formula (V) (hereafter called "compound (V)").

Chem. 6

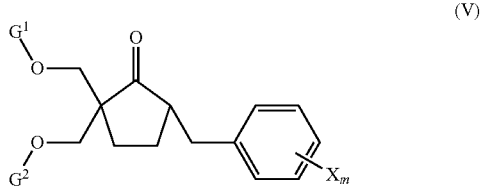

(V)

In formula (V), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; $G^1$ and $G^2$ each represents a protecting group that dissociates under acidic conditions, $G^1$ and $G^2$ may be the same or different, and $G^1$ and $G^2$ may bond with one another to form a ring.

First, compound (V) will be described.
1. Compound (V)
Compound (V) is an intermediate compound of a compound that can be suitably used as an active ingredient for agricultural and horticultural chemicals and industrial material protectants.

In formula (V), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group.

Specific examples of halogen atoms in X include fluorine atoms, chlorine atoms, bromine atoms, and iodine atoms. Of these, fluorine atoms, chlorine atoms, and bromine atoms are preferable, and chlorine atoms are more preferable.

Specific examples of alkyl groups having from 1 to 4 carbons in X include methyl groups, ethyl groups, n-propyl groups, isopropyl groups, n-butyl groups, isobutyl groups, sec-butyl groups, and tert-butyl groups. Of these, alkyl groups having from 1 to 3 carbons are preferable, and alkyl groups having 1 or 2 carbons are more preferable. Methyl groups are even more preferable.

The haloalkyl group having from 1 to 4 carbons in X is an alkyl group substituted with 1 or 2 or more of the same or different halogen atoms, examples of which include dichloromethyl groups, trichloromethyl groups, 2-chloroethyl groups, 1-chloroethyl groups, 2,2-dichloroethyl groups, 1,2-dichloroethyl groups, 2,2,2-trichloroethyl groups, 3-chloropropyl groups, 2,3-dichloropropyl groups, 1-chloro-1-methylethyl groups, 2-chloro-1-methylethyl groups, 2-chloropropyl groups, 4-chlorobutyl groups, fluoromethyl groups, difluoromethyl groups, trifluoromethyl groups, 2-fluoroethyl groups, 1-fluoroethyl groups, 2,2-difluoroethyl groups, 1,2-difluoroethyl groups, 2,2,2-trifluoroethyl groups, 3-fluoropropyl groups, 2,3-difluoropropyl groups, 1-fluoro-1-methylethyl groups, 2-fluoro-1-methylethyl groups, 2-fluoropropyl groups, 3,3,3-trifluoropropyl groups, 2,2,3,3-tetrafluoropropyl groups, 2,2,3,3,3-pentafluoropropyl groups, 4-fluorobutyl groups, dibromomethyl groups, tribromomethyl groups, 2-bromoethyl groups, 2,2-dibromoethyl groups, 1,2-dibromoethyl groups, 2,2,2-tribromoethyl groups, 3-bromopropyl groups, 2,3-dibromopropyl groups, 1-bromo-1-methylethyl groups, 2-bromo-1-methylethyl groups, 2-bromopropyl groups, diiodomethyl groups, 2,2-diiodoethyl groups, 1,2-diiodoethyl groups, 2,2,2-triiodoethyl groups, 2,3-diiodopropyl groups, 1-iodo-1-methylethyl groups, 2-iodo-1-methylethyl groups, and the like. Of these, haloalkyl groups having from 1 to 3 carbons are preferable, and haloalkyl groups having 1 or 2 carbons are more preferable. Trihaloalkyl groups having 1 carbon are even more preferable.

Examples of alkoxy groups having from 1 to 4 carbons in X include methoxy groups, ethoxy groups, n-propoxy groups, and the like. Of these, alkoxy groups having from 1 to 3 carbons are preferable, and alkoxy groups having 1 or 2 carbons are more preferable. Methoxy groups are even more preferable.

The haloalkoxy group having from 1 to 4 carbons in X is an alkoxy group substituted with 1 or 2 or more of the same or different halogen atoms, examples of which include trifluoromethoxy groups, difluoromethoxy groups, 1,1,2,2,2-pentafluoroethoxy groups, 2,2,2-trifluoroethoxy groups, and the like. Of these, haloalkoxy groups having from 1 to 3 carbons are preferable, and haloalkoxy groups having 1 or 2 carbons are more preferable. Dihalomethoxy groups and trihalomethoxy groups having 1 carbon are even more preferable.

X is preferably a halogen atom, an alkyl group having from 1 to 3 carbons, a haloalkyl group having from 1 to 3 carbons, an alkoxy group having from 1 to 3 carbons, or a haloalkoxy group having from 1 to 3 carbons, more preferably a halogen atom, a methyl group, a trifluoromethyl group, a trifluoromethoxy group, or a difluoromethoxy group, even more preferably a halogen atom, and particularly preferably a chlorine atom.

In formula (V), m is an integer from 0 to 5. m is preferably an integer from 0 to 3, more preferably an integer from 0 to 2, and even more preferably 0 or 1. When m is an integer of 2 or greater, a plurality of X moieties may be the same or different from one another. When m is an integer of 1 or greater, X may be positioned at any of the positions 2 to 6 of a benzene ring. When m is 1, a position forming 4-substituted benzyl is preferable.

In formula (V), $G^1$ and $G^2$ are each a protecting group that dissociates under acidic conditions. $G^1$ and $G^2$ are protecting groups that protect hydroxy groups. $G^1$ and $G^2$ may be the same or different from one another. In addition, $G^1$ and $G^2$ may bond with one another to form a ring. $G^1$ and $G^2$ are not particularly limited as long as they dissociate under acidic conditions.

When $G^1$ and $G^2$ do not bond, compound (V) can be expressed by the following general formula (Vb).

Chem. 7

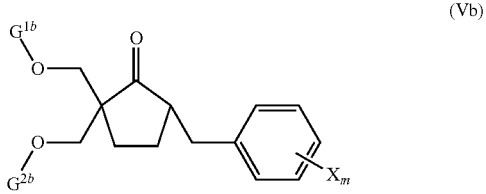

(Vb)

In formula (Vb), X and m are each the same as X and m in formula (V).

In formula (Vb), $G^{1b}$ and $G^{2b}$ are each independently an alkoxymethyl group having from 1 to 4 carbons in the alkoxy moiety, an alkoxyethyl group having from 1 to 4 carbons in the alkoxy moiety, an alkyl group having from 1 to 4 carbons, an allyl group, a substituted or unsubstituted benzyl group, a substituted or unsubstituted tetrahydropyranyl group, or a substituted or unsubstituted tetrahydrofuranyl group.

Examples of alkoxymethyl groups having from 1 to 4 carbons in the alkoxy moiety in $G^{1b}$ and $G^{2b}$ include methoxymethyl groups, ethoxymethyl groups, and the like.

Examples of alkoxyethyl groups having from 1 to 4 carbons in the alkoxy moiety in $G^{1b}$ and $G^{2b}$ include 1-ethoxyethyl groups, 1-methyl-1-methoxyethyl groups, and the like.

Specific examples of alkyl groups having from 1 to 4 carbons in $G^{1b}$ and $G^{2b}$ include methyl groups, ethyl groups, n-propyl groups, isopropyl groups, n-butyl groups, isobutyl groups, sec-butyl groups, and tert-butyl groups.

When the benzyl groups, tetrahydropyranyl groups, and tetrahydrofuranyl groups have substituents, examples of these substituents include bromine atoms, chlorine atoms, fluorine atoms, methoxy groups, trifluoromethyl groups, nitro groups, nitrile groups, phenyl groups, and the like.

On the other hand, examples of protecting groups when $G^1$ and $G^2$ bond with one another to form a ring include, but are not limited to, methylene acetal, ethylidene acetal, t-butylmethylidene ketal, 1-t-butylethylidene ketal, 1-phenylethylidene ketal, acrolein acetal, isopropylidene ketal (acetonide), cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene ketal, 2-nitrobenzylidene acetal, 4-nitrobenzylidene acetal, mesitylene acetal, 1-naphthaldehyde acetal, benzophenone ketal, camphor ketal, menthone, methoxymethylene acetal, ethoxymethylene acetal, dimethoxymethylene orthoester, 1-methoxyethylidene orthoester, 1-ethoxyethylidene orthoester, methylidene orthoester, phthalide orthoester, 1,2-dimethoxyethylidene orthoester, α-methoxybenzylidene orthoester, 2-oxacyclopentylidene orthoester, butane-2,3-bis-acetal, cyclohexane-1,2-diacetal, bis-dihydropyran ketal, di-t-butylsilylene, 1,3-(1,1,3,3-tetraisopropyl)disiloxanilidene, 1,1,3,3-tetra-t-butoxydisiloxanilidene, and the like.

Of these, when $G^1$ and $G^2$ bond with one another to form a ring, compound (V) is preferably a compound represented by the following general formula (Va).

Chem. 8

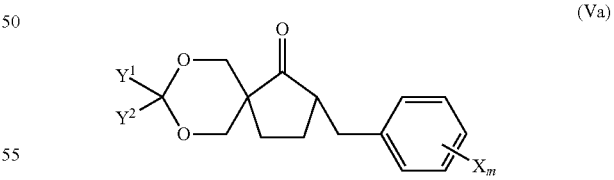

(Va)

In formula (Va), X and m are each the same as X and m in formula (V).

In formula (Va), $Y^1$ and $Y^2$ are each independently a hydrogen atom, an alkyl group having from 1 to 4 carbons, an alkenyl group having from 1 to 4 carbons, a phenyl group, a naphthyl group, or a benzyl group. The phenyl parts of the phenyl groups, naphthyl groups, and benzyl groups of $Y^1$ and $Y^2$ may be further substituted with alkyl groups having from 1 to 4 carbons such as methyl groups and ethyl groups; alkoxy groups having from 1 to 4 carbons such as methoxy groups and ethoxy groups; nitro groups; or halogen atoms such as fluorine atoms and chlorine atoms. In addition, $Y^1$ and $Y^2$ may bond with one another to form a ring. Of these, $Y^1$ and $Y^2$ are more preferably independently hydrogen atoms or alkyl groups having from 1 to 4 carbons such as methyl groups, ethyl groups, and n-propyl groups and even more preferably independently alkyl groups having from 1 to 4 carbons. It is particularly preferable for both $Y^1$ and $Y^2$ to be methyl groups.

2. Compound (V) Production Method

The production method for compound (V) of the present invention is a method comprising a step of obtaining a compound represented by the following general formula (II) (hereafter called "compound (II)") by reacting a compound represented by the following general formula (I) (hereafter called "compound (I)") with an acid (step 1).

Chem. 9

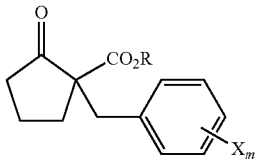

(I)

In formula (I), X and m are each the same as X and m in formula (V), and R is an alkyl group having from 1 to 4 carbons.

Chem. 10

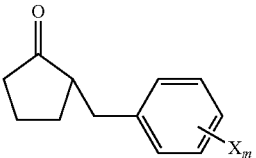

(II)

In formula (II), X and m are each the same as X and m in formula (V).

The other steps of the production method for compound (V) of the present invention are not particularly limited as long as the method includes step 1, but an example of a preferable method is a method which further includes steps 2 to 4 in addition to step 1, as illustrated in the following reaction scheme 1. An embodiment of the production method for compound (V) will be described using the reaction illustrated in reaction scheme 1 as an example.

(REACTION SCHEME 1)

Chem. 11

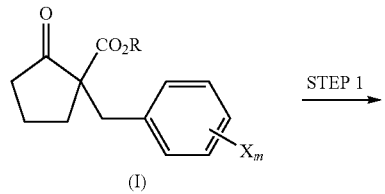

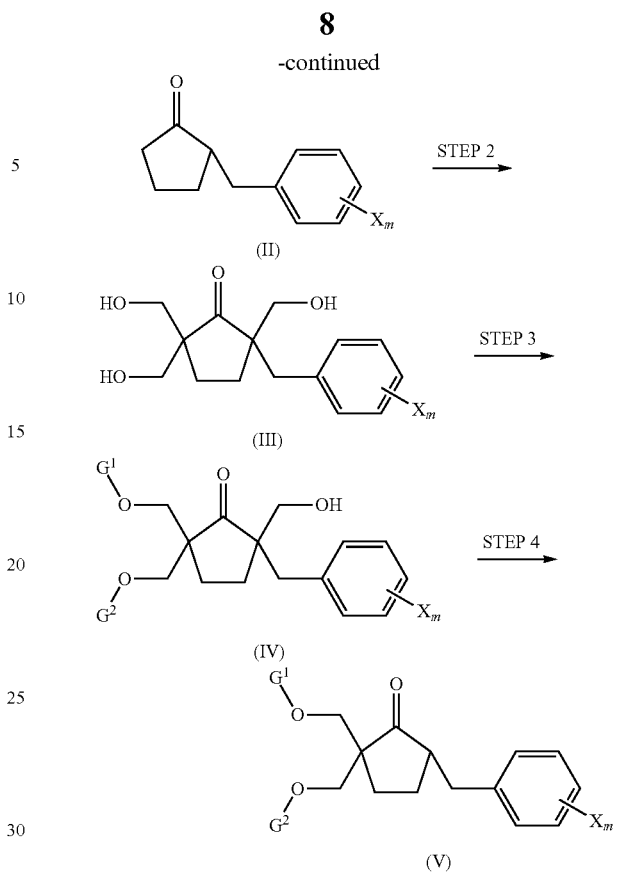

Step 1: Hydrolysis/Decarboxylation Step

Step 1 is a step of performing hydrolysis/decarboxylation to obtain compound (II) by reacting compound (I) with an acid.

In formula (I), X and m are each the same as X and m in formula (V).

In formula (I), R is an alkyl group having from 1 to 4 carbons. Specific examples of alkyl groups having from 1 to 4 carbons in R include methyl groups, ethyl groups, n-propyl groups, isopropyl groups, n-butyl groups, isobutyl groups, sec-butyl groups, and tert-butyl groups. Of these, alkyl groups having from 1 to 3 carbons are preferable, and alkyl groups having 1 or 2 carbons are more preferable. Methyl groups are even more preferable.

A compound produced by a publicly known method (for example, the method described in Patent Document 1) may be used as compound (I).

Examples of acids in step 1 include inorganic acids such as hydrochloric acid, hydrobromic acid, hydroiodic acid, hydrofluoric acid, chloric acid, perchloric acid, sulfuric acid, nitric acid, phosphoric acid, hexafluorophosphoric acid, and tetrafluoroboric acid; and organic acids such as acetic acid, trifluoroacetic acid, formic acid, benzoic acid, methanesulfonic acid, ethanesulfonic acid, benzenesulfonic acid, p-toluenesulfonic acid, p-chlorobenzenesulfonic acid, trifluoromethanesulfonic acid, and camphorsulfonic acid.

The amount of acid used is, for example, from 0 times to 20 times (excluding 0 times) the molar quantity of compound (I) and is preferably from 0.001 times to 10 times the molar quantity of compound (I).

The reaction temperature is, for example, from −20° C. to 200° C. and is preferably from 0° C. to 150° C. The reaction time is, for example, from 0.1 hours to several days and is preferably from 0.5 hours to 2 days.

The solvent used in step 1 is not particularly limited, and examples of solvents include water, toluene, and the like.

Here, the advantages of the production method for compound (V) including step 1 will be described. Using the method described in Patent Document 1 as a reference, an example of a method for producing compound (V) from compound (I) is the following reaction scheme 2. Here, X, m, R, $G^1$, and $G^2$ in compounds illustrated in reaction scheme 2 are the same as X, m, R, $G^1$, and $G^2$ described above.

(REACTION SCHEME 2)

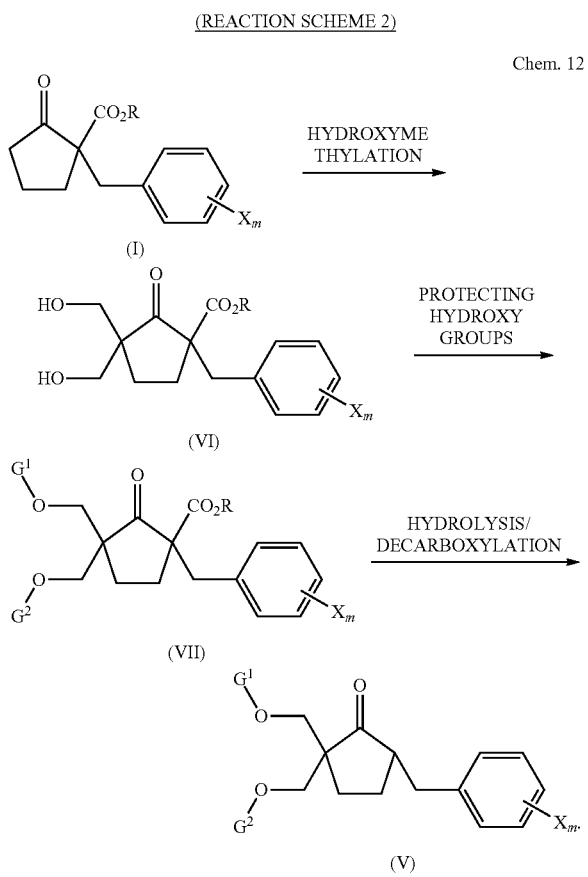

In reaction scheme 2, $G^1$ and $G^2$ in the compound represented by general formula (VII) (hereafter called "compound (VII)") are protecting groups that dissociate under acidic conditions. Therefore, the hydrolysis and decarboxylation reactions in the step of producing compound (V) from compound (VII) must be performed under basic conditions. However, as a result of conducting various investigations, it was found that when compound (VII) is hydrolyzed and decarboxylated under basic conditions, the yield of compound (V) decreases due to the occurrence of side reactions involving the opening of cyclopentane rings.

In contrast, in the production method for compound (V) including step 1 of the present invention, hydrolysis and decarboxylation are performed under acidic conditions by undergoing step 1 before introducing protecting groups. As a result, it is possible to avoid reactions in which side reactions involving the opening of cyclopentane rings may occur in the hydrolysis/decarboxylation step and subsequent steps. Accordingly, the production method for compound (V) of the present invention is excellent from the perspective of the yield of compound (V) since by-products are unlikely to be generated.

Step 1 is a novel reaction route. Therefore, the present invention also provides a production method for compound (II) by means of step 1.

Step 2: Hydroxymethylation Step

Step 2 is a step of hydroxymethylating compound (II) by reacting compound (II) with formaldehyde or a formaldehyde derivative to obtain a compound represented by the following general formula (III) (hereafter called "compound (III)").

Chem. 13

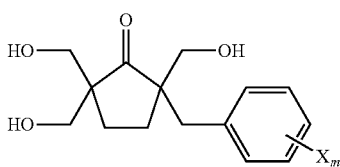

In formula (III), X and m are each the same as X and m in formula (V).

Examples of formaldehyde derivatives include paraformaldehyde, 1,3,5-trioxane, formaldehyde dialkyl acetal, and the like.

The amount of formaldehyde or a formaldehyde derivative used is, for example, from 1 time to 100 times the molar quantity of compound (II) and is preferably from 2 times to 50 times the molar quantity of compound (II).

The reaction of step 2 is preferably performed in a solvent in the presence of a base. Examples of bases include carbonates of alkali metals such as sodium carbonate, sodium hydrogen carbonate, potassium carbonate, and potassium hydrogen carbonate; hydroxides of alkali metals such as sodium hydroxide and potassium hydroxide; organic bases such as triethylamine and diisopropylethylamine; and the like.

The amount of the base used is, for example, from 0.01 times to 100 times the molar quantity of compound (II) and is preferably from 0.1 times to 50 times the molar quantity of compound (II).

The reaction temperature is, for example, from 0° C. to 200° C. and is preferably from 0° C. to the reflux point. The reaction time is, for example, from 0.1 hours to several days and is preferably from 0.2 hours to 3 days.

The solvent used in step 2 is not particularly limited, but examples include alcohols such as methanol, ethanol, and isopropyl alcohol; ethers such as diethyl ether, tetrahydrofuran, and dioxane; aromatic hydrocarbons such as benzene, toluene, and xylene; water; and the like. These may also be mixed and used as necessary. Here, if the reaction system forms a dual phase, it is preferable to use a phase transfer catalyst such as, for example, a commonly used quaternary ammonium salt (for example, benzyltriethylammonium chloride).

Compound (III) obtained in step 2 is a novel compound. Therefore, the present invention also provides compound (III) and a production method thereof.

Step 3: Protection Step

Step 3 is a step of obtaining a compound represented by the following general formula (IV) (hereafter called "compound (IV)") by protecting some of the hydroxy groups of compound (III) with protecting groups. Here, the protecting groups that are introduced are protecting groups that dissociate under acidic conditions.

Chem. 14

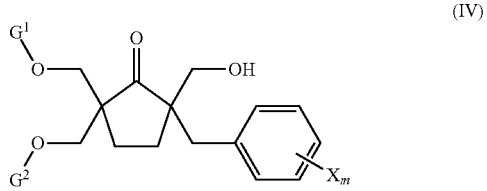

(IV)

In formula (IV), X, m, $G^1$, and $G^2$ are each the same as X, m, $G^1$, and $G^2$ in formula (V).

The introduction of $G^1$ and $G^2$ is realized by reacting a compound for introducing protecting groups with compound (III) in the presence of an acid.

The compound for introducing protecting groups is not particularly limited as long as the compound is capable of introducing the protecting groups described above, but examples include acetone dimethyl acetal, isobutene, acetone, dialkoxymethane, and the like.

Examples of the acid used in step 3 include inorganic acids such as hydrochloric acid, phosphoric acid, and sulfuric acid, organic acids such as p-toluenesulfonic acid, trifluoroacetic acid, and methanesulfonic acid, and the like.

The amount of acid used is, for example, from 0 times to 10 times (excluding 0 times) the molar quantity of compound (III) and is preferably from 0.001 times to 5 times the molar quantity of compound (III).

The amount of the compound used to introduce protecting groups can be set appropriately in accordance with the types of the compound, the acid used, and the compound (III), but the amount is, for example, from 0.5 times to 50 times the molar quantity of compound (III) and is preferably from 0.8 times to 10 times the molar quantity of compound (III).

The solvent used in step 3 is not particularly limited, but examples include acetone, toluene, tetrahydrofuran, and the like.

When (a) an alkoxymethyl group is introduced, (b) a t-butyl group is introduced, or (c) two hydroxy groups are simultaneously protected with acetal or ketal as a protecting group, the respective methods described below are preferably used.

First, the case in which (a) an alkoxymethyl group is introduced will be described.

When an alkoxymethyl group is introduced, it is preferable to use a method of subjecting the hydroxy groups in compound (III) to acetal exchange using formaldehyde dialkyl acetal.

Examples of acids that can be used in this case include inorganic acids such as hydrochloric acid, phosphoric acid (including compounds in which acidic moieties are produced by the addition of alcohol or water, such as diphosphorus pentaoxide), and sulfuric acid, and organic acids such as p-toluenesulfonic acid. Formaldehyde dialkyl acetal is preferably used in the presence of an acid in a solvent or without a solvent. It is more preferable to add a compound capable of removing alcohol that is produced (for example, diphosphorus pentaoxide).

The amount of formaldehyde dialkyl acetal used is, for example, from 0.5 times to 50 times the molar quantity of compound (III) and is preferably from 0.8 times to 10 times the molar quantity of compound (III). The amount of acid used is, for example, from 0.01 times to 10 times and is preferably from 0.05 times to 5 times the molar quantity of compound (III).

The reaction temperature is, for example, from 0° C. to 250° C. and is preferably from 0° C. to 150° C. The reaction time is, for example, from 0.1 hours to several days and is preferably from 0.5 hours to 2 days.

Next, the case in which (b) a t-butyl group is introduced will be described.

When a t-butyl group is introduced, it is preferable to use a method of introducing a t-butyl group into the hydroxy groups in compound (III) using isobutene.

Examples of acids that can be used in this case include inorganic acids such as hydrochloric acid, phosphoric acid, and sulfuric acid, and organic acids such as p-toluenesulfonic acid and trifluoroacetic acid. It is preferable to react compound (III) and isobutene in a solvent.

The amount of isobutene used is, for example, from 0.5 times to 100 times the molar quantity of compound (III) and is preferably from 0.8 times to 20 times the molar quantity of compound (III). The amount of acid used is, for example, from 0.01 times to 10 times and is preferably from 0.05 times to 5 times the molar quantity of compound (III).

The reaction temperature is, for example, from 0° C. to 200° C. and is preferably from 0° C. to 100° C. The reaction time is, for example, from 0.1 hours to several days and is preferably from 0.5 hours to 2 days.

Finally, the case in which (c) two hydroxy groups are simultaneously protected with acetal or ketal will be described.

When two hydroxy groups are simultaneously protected with acetal or ketal, it is preferable to use a method of reacting an appropriate aldehyde or ketone with compound (III) in the presence of an acid. This makes it possible to introduce protecting groups in which $G^1$ and $G^2$ bond with one another to form a ring.

When $G^1$ and $G^2$ bond with one another to form a ring, compound (IV) can be expressed, for example, by the following general formula (IVa).

Chem. 15

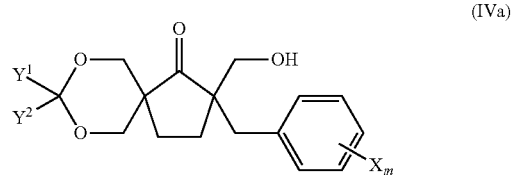

(IVa)

In formula (IVa), X, m, $Y^1$ and $Y^2$ are each the same as X, m, $Y^1$ and $Y^2$ in formula (Va).

When two hydroxy groups are simultaneously protected with acetal or ketal and, for example, the protecting group that is introduced is isopropylidene ketal, it is preferable to react compound (III) with acetone or acetone dimethyl acetal in the presence of an acid in a solvent. Examples of acids that can be used in this case include inorganic acids such as hydrochloric acid, phosphoric acid, and sulfuric acid, and organic acids such as p-toluenesulfonic acid and trifluoroacetic acid.

The amount of acetone dimethyl acetal used is, for example, from 0.5 times to 50 times the molar quantity of compound (III) and is preferably from 0.8 times to 10 times the molar quantity of compound (III). The amount of acid used is, for example, from 0 times to 100 times (excluding 0 times) the molar quantity of compound (III) and is preferably from 0.001 times to 50 times the molar quantity of compound (III).

Compound (IV) obtained in step 3 is a novel compound. Therefore, the present invention also provides compound (IV) and a production method thereof.

Step 4: Dehydroxymethylation Step

Step 4 is a step of obtaining compound (V) by dehydroxymethylating compound (IV) under basic conditions.

The reaction in step 4 is preferably performed in a solvent in the presence of a base. Examples of bases include carbonates of alkali metals such as sodium carbonate, sodium hydrogen carbonate, potassium carbonate, and potassium hydrogen carbonate; carbonates of alkali earth metals such as calcium carbonate and barium carbonate; hydroxides of alkali metals such as sodium hydroxide and potassium hydroxide; alkali metals such as lithium, sodium, and potassium; alkoxides of alkali metals such as sodium methoxide, sodium ethoxide, and potassium t-butoxide; alkali metal hydride compounds such as sodium hydride, potassium hydride, and lithium hydride; organic metal compounds of alkali metals such as n-butyl lithium; alkali metal amides such as lithium diisopropyl amide; organic amines such as triethylamine, pyridine, 4-dimethylaminopyridine, N,N-dimethylaniline, and 1,8-diazabicyclo-7-[5.4.0]undecene; and the like. The amount of the base used is, for example, from 0.01 times to 200 times the molar quantity of compound (IV) and is preferably from 0.1 times to 100 times the molar quantity of compound (IV).

Water or the like can be used as the solvent in step 4.

The reaction temperature is, for example, from −50° C. to the reflux point and is preferably from 0° C. to the reflux point. The reaction time is, for example, from 0.1 hours to 10 days and is preferably from 0.2 hours to several days.

Compound (V) obtained above is suitably used in the synthesis of an azole derivative, which is an active ingredient of agricultural and horticultural chemicals and industrial material protectants described in Patent Document 1. The specific production of an azole derivative from compound (V) can be realized in accordance with the method described in Patent Document 1.

SUMMARY

The production method for a cyclopentanone derivative according to the present invention preferably further includes a step of obtaining compound (III) by reacting compound (II) with formaldehyde or a formaldehyde derivative.

The production method for a cyclopentanone derivative according to the present invention preferably further includes a step of obtaining compound (IV) by protecting some of the hydroxy groups of compound (III) with protecting groups that dissociate under acidic conditions.

The production method for a cyclopentanone derivative according to the present invention preferably further includes a step of obtaining compound (V) by dehydroxymethylating compound (IV) under basic conditions.

In addition, compound (V) is sometimes preferably compound (Va) in the production method of the present invention.

In formula (Va), $Y^1$ and $Y^2$ are more preferably each independently a hydrogen atom or an alkyl group having from 1 to 4 carbons.

In formula (Va), it is even more preferable for both $Y^1$ and $Y^2$ to be methyl groups.

In addition, compound (V) is sometimes preferably compound (Vb) in the production method of the present invention.

In formula (V) of the production method of the present invention, m is preferably an integer from 0 to 3, and when m is 1 or greater, X is preferably a halogen atom, an alkyl group having from 1 to 3 carbons, a haloalkyl group having from 1 to 3 carbons, an alkoxy group having from 1 to 3 carbons, or a haloalkoxy group having from 1 to 3 carbons.

In formula (V) of the production method of the present invention, m is more preferably an integer from 0 to 2, and when m is 1 or 2, X is more preferably a halogen atom.

Embodiments of the present invention will be described in further detail hereinafter using practical examples. Of course, the present invention is not limited to the practical examples below, and it goes without saying that various modes are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents cited in this specification are hereby incorporated by reference.

EXAMPLES

In this practical example, 2-(4-chlorobenzyl)-8,8-dimethyl-7,9-dioxaspiro[4,5]decan-1-one (compound (5)) was synthesized from methyl 1-(4-(chlorobenzyl)-2-oxocyclopentane carboxylate (compound (1)) in accordance with reaction scheme 3 illustrated below. Furthermore, 5-(4-chlorobenzyl)-2,2-bis(hydroxymethyl)-1-(1H-1,2,4-triazol-1-ylmethyl)cyclopentanol (compound (7)) was synthesized from compound (5).

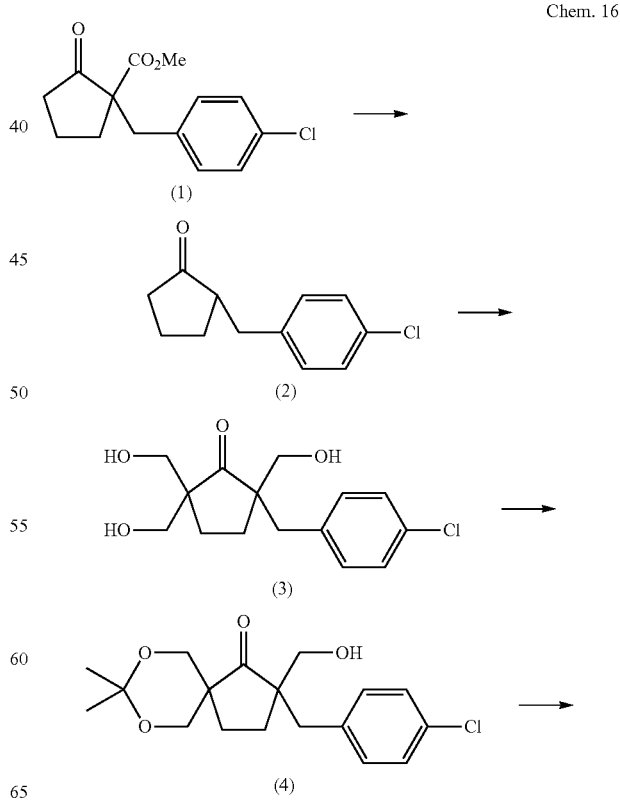

(REACTION SCHEME 3)

Chem. 16

-continued

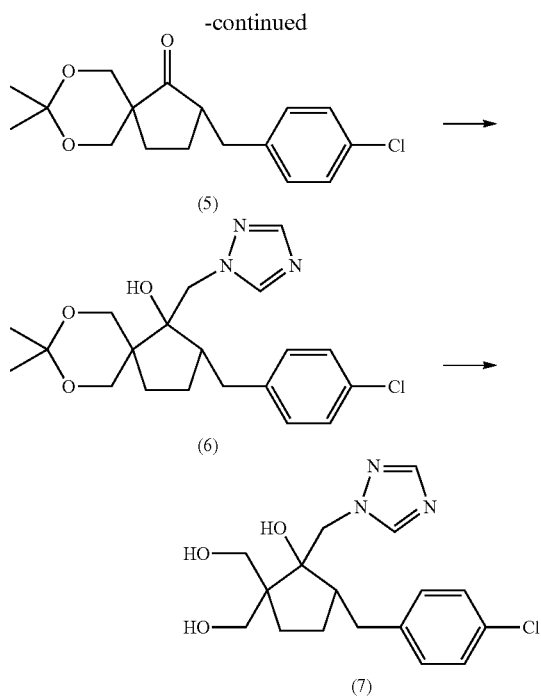

Production Example

Synthesis of Compound (5)

(1) Synthesis of 2-(4-chlorobenzyl)-cyclopentanone (Compound (2))

First, p-toluenesulfonic acid monohydrate (3.57 mg) and water (277 μL) were added to compound (1) (1.00 g) and stirred for 3 hours at 110° C. Following the completion of the reaction, after a saturated sodium hydrogen carbonate aqueous solution was added and stirred for a certain amount of time, the solution was extracted with ethyl acetate. Furthermore, after this was washed with a saturated sodium hydrogen carbonate aqueous solution and then saturated brine, the organic layer was dried with anhydrous sodium sulfate. The solvent was distilled out, and the residue was purified by silica gel column chromatography to obtain 783 mg of the target product (compound (2)) as a colorless, oily substance.

Yield: 783 mg
Yield rate: 100%
$^1$H-NMR (400 MHz, CDCl$_3$): δ=1.47-1.57 (1H, m), 1.68-1.80 (1H, m), 1.92-2.00 (1H, m), 2.04-2.13 (2H, m), 2.28-2.38 (2H, m), 2.54 (1H, dd, J=14.0, 9.1 Hz), 3.09 (1H, dd, J=14.0, 4.3 Hz), 7.08-7.11 (2H, m), 7.23-7.25 (2H, m).

(2) Synthesis of 2-(4-chlorobenzyl)-2,5,5-tris-hydroxymethyl-cyclopentanone (Compound (3))

Compound (2) (3.01 g) was dissolved in triethylamine (3.01 mL). Next, a 37% formaldehyde aqueous solution (4.34 mL) was added and stirred for 3.5 hours at 50° C. Water (6 mL) and then concentrated hydrochloric acid (3 mL) were slowly added to this solution, and the solution was stirred overnight at room temperature. Following the completion of the reaction, the solution was extracted with ethyl acetate, and after the solution was washed with water and then saturated brine, the organic layer was dried with anhydrous sodium sulfate. The solvent was distilled out to obtain 4.78 g of the target product (compound (3)) as a colorless crystal.

Crude yield: 4.78 g
Crude yield rate: 100%
$^1$H-NMR (400 MHz, CDCl$_3$): δ=1.61-1.70 (1H, m), 1.90-1.98 (3H, m), 2.16-2.19 (1H, m), 2.41-2.44 (1H, m), 2.52-2.55 (1H, m), 2.68 (1H, d, J=13.4 Hz), 2.84 (1H, d, J=13.4 Hz), 3.34-3.43 (2H, m), 3.53 (1H, dd, J=10.8, 4.2 Hz), 3.65-3.69 (2H, m), 3.81 (1H, dd, J=10.9, 5.4 Hz), 7.06-7.09 (2H, m), 7.24-7.27 (2H, m).

(3) Synthesis of 2-(4-chlorobenzyl)-2-hydroxymethyl-8,8-dimethyl-7,9-dioxaspiro[4,5]decan-1-one (Compound (4))

Compound (3) (4.78 g) was dissolved in a mixture of acetone dimethyl acetal (9.80 mL) and acetone (2 mL). Next, p-toluenesulfonic acid monohydrate (76.1 mg) was added and stirred overnight at room temperature. Following the completion of the reaction, sodium hydrogen carbonate (53.8 mg) was added and stirred for a certain amount of time, and the solvent was distilled out until the volume was reduced by half. Water was further added to the solution and stirred for a certain amount of time. This was extracted with toluene, and after the solution was washed with a saturated sodium hydrogen carbonate aqueous solution and then saturated brine, the organic layer was dried with anhydrous sodium sulfate. The solvent was distilled out, and the residue was purified by silica gel column chromatography to obtain 3.12 g of the target product (compound (4)) as a colorless crystal.

Yield: 3.12 g
Yield rate: 63.9% (yield from compound (2))
$^1$H-NMR (400 MHz, CDCl$_3$): δ=1.34 (3H, s), 1.46 (3H, s), 1.70-1.77 (1H, m), 1.87-1.97 (3H, m), 2.14-2.20 (1H, m), 2.61 (1H, d, J=13.3 Hz), 2.84 (1H, d, J=13.3 Hz), 2.97 (1H, dd, J=11.4, 2.6 Hz), 3.47 (1H, dd, J=10.8, 3.8 Hz), 3.53 (1H, dd, J=11.4, 2.6 Hz), 3.63 (1H, dd, J=10.8, 7.5 Hz), 3.82 (1H, d, J=11.4 Hz), 3.91 (1H, d, J=11.4 Hz), 7.01-7.04 (2H, m), 7.22-7.26 (2H, m).

(4) Synthesis of Compound (5)

Compound (4) (103 mg) was dissolved in toluene (1 mL). Next, a 25% sodium hydroxide aqueous solution (3 mL) was added and stirred for 3 hours at 120° C. Following the completion of the reaction, after water was added and stirred for a certain amount of time, this was extracted with toluene. Furthermore, after the solution was washed with saturated brine, the organic layer was dried with anhydrous sodium sulfate. The solvent was distilled out, and the residue was purified by silica gel column chromatography to obtain 90.9 mg of the target product (compound (5)) as a colorless crystal.

Yield: 90.9 mg
Yield rate: 96.8%
$^1$H-NMR (400 MHz, CDCl$_3$): δ=1.38 (3H, s), 1.49 (3H, s), 1.49-1.59 (1H, m), 1.80-1.88 (1H, m), 2.04-2.12 (1H, m), 2.39-2.50 (2H, m), 2.60 (1H, dd, J=13.9, 8.4 Hz), 3.00 (1H, dd, J=13.9, 4.5 Hz), 3.24 (1H, dd, J=11.4, 2.6 Hz), 3.47 (1H, dd, J=11.4, 2.6 Hz), 3.78 (1H, dd, J=11.4, 1.6 Hz), 4.06 (1H, d, J=11.4 Hz), 7.04-7.07 (2H, m), 7.22-7.25 (2H, m).

Reference Production Example

Synthesis of Compound (7)

(1) Synthesis of 2-(4-chlorobenzyl)-8,8-dimethyl-1-(1H-1,2,4-triazol-1-ylmethyl)-7,9-dioxaspiro[4,5]decan-1-ol (Compound (6))

First, after NaH (0.91 g (ca. 60% in mineral oil), 0.0228 mol) was suspended in N-methylpyrrolidone (NMP) (8 mL), 1,2,4-triazole (1.67 g) was added and stirred for 0.5 hours to produce a sodium salt. Next, compound (5) (5.00 g) was added. After this was heated to approximately 90° C. (bath temperature), trimethylsulfoxonium bromide (TMSOB) (4.20 g) and t-BuONa (0.77 g) were intermittently added over the course of 1.5 hours and then reacted for 1.5 hours. After the reaction solution was further heated to approximately 125° C. (bath temperature) and reacted for 1 hour, saturated ammonium chloride and water were added to the reaction solution and then extracted with ethyl acetate. After the organic layer was dried with anhydrous sodium sulfate, the solvent was distilled out, and the crude product was purified by silica gel column chromatography to obtain the target product (compound (6)) as an isomer mixture consisting of a 93:7 ratio of the cis-form to the trans-form.

Yield: 4.68 g
Yield rate: 74.3%
Cis-Form
$^1$H-NMR (CDCl$_3$) δ=1.37 (3H, s), 1.49 (3H, s), 1.53-1.57 (1H, m), 1.83-1.88 (1H, m), 2.04-2.10 (1H, m), 2.39-2.50 (2H, m), 2.60 (1H, dd, J=14.0, 8.4 Hz), 3.00 (1H, dd, J=14.0, 4.4 Hz), 3.24 (1H, dd, J=11.4, 2.6 Hz), 3.47 (1H, dd, J=11.4, 2.6 Hz), 3.78 (1H, dd, J=11.4, 2.0 Hz), 4.14 (1H, d, J=11.4 Hz), 7.02-7.10 (2H, m), 7.21-7.27 (2H, m).

Trans-Form $^1$H-NMR (CDCl$_3$) δ=1.22-1.60 (3H, m), 1.38 (3H, s), 1.47 (3H, s), 1.65-1.80 (1H, m), 2.10-2.21 (2H, m), 2.72-2.86 (1H, m), 3.67 (1H, d, J=12.0 Hz), 3.75 (1H, d, J=12.5 Hz), 3.97 (1H, dd, J=12.5, 2.5 Hz), 4.25 (1H, dd, J=12.0, 2.5 Hz), 4.65-4.75 (3H, m), 6.90 (2H, d, J=8.3 Hz), 7.13-7.23 (3H, m), 8.00 (1H, s). 8.39 (1H, s).

(2) Synthesis of Compound (7)

Compound (6) (8.98 g) was dissolved in a mixture of methanol (30 mL) and a 6N hydrochloric acid aqueous solution (40 mL) and stirred for 4 hours at room temperature. After water was added to the mixture, the mixture was neutralized with sodium carbonate and sodium bicarbonate. Next, after this was extracted with ethyl acetate, the organic layer was washed with saturated brine. After the organic layer was dried with anhydrous sodium sulfate, the solvent was distilled out to obtain the target product (compound (7)) as an isomer mixture.

Yield: 7.96 g
Yield rate: 98.7%
Cis-Form (Trans-Form Omitted)
$^1$H-NMR (CDCl$_3$) δ=1.20-1.25 (1H, m), 1.43-1.61 (5H, m), 2.05-2.15 (2H, m), 2.40-2.48 (1H, m), 3.63 (1H, d, J=11.2 Hz), 3.75 (1H, d, J=14.0 Hz), 3.77 (1H, d, J=14.0 Hz), 3.86 (1H, d, J=11.2 Hz), 4.45 (1H, d, J=14.3 Hz), 4.75 (1H, d, J=14.3 Hz), 4.84 (1H, brs), 6.97 (2H, d, J=8.4 Hz), 7.20 (2H, d, J=8.4 Hz), 8.00 (1H, s), 8.24 (1H, s).

INDUSTRIAL APPLICABILITY

The present invention can be used in the production of a 2-benzyl-5,5-bis(hydroxymethyl)-cyclopentanone derivative having a protected hydroxy group serving as a raw material for an agricultural chemical or the like.

The invention claimed is:
1. A production method for a compound represented by formula (III), comprising:
obtaining a compound represented by formula (III) below by reacting a compound represented by formula (II) with a compound selected from the group consisting of a formaldehyde, paraformaldehyde, 1,3,5-trioxane, and formaldehyde dialkyl acetal:

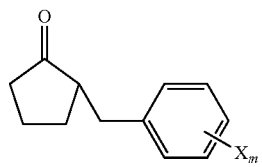

(II)

in formula (II), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; and

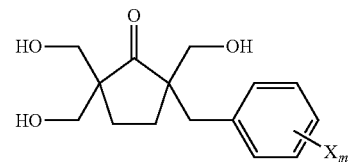

(III)

in formula (III), X and m are each the same as X and m in formula (II).

2. A production method for a compound represented by formula (IV), comprising:
obtaining a compound represented by formula (IV) below by reacting a compound represented by formula (III) with protecting groups that dissociate under acidic conditions:

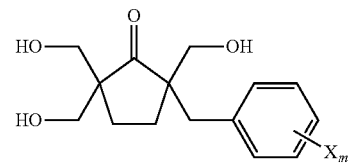

(III)

in formula (III), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; and

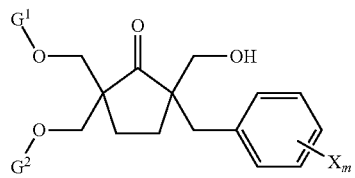

(IV)

in formula (IV), X and m are each the same as X and m in formula (III); and $G^1$ and $G^2$ each represents a protecting group that dissociates under acidic conditions, $G^1$ and $G^2$ may be the same or different, and $G^1$ and $G^2$ may bond with one another to form a ring.

3. A production method for a cyclopentanone derivative represented by formula (V), comprising:

obtaining a compound represented by formula (V) by dehydroxymethylating a compound represented by formula (IV) under basic conditions:

Chem. 1

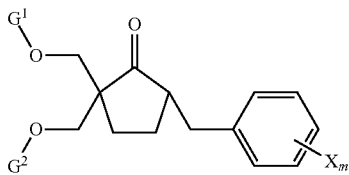
(V)

in formula (V), X is a halogen atom, an alkyl group having from 1 to 4 carbons, a haloalkyl group having from 1 to 4 carbons, an alkoxy group having from 1 to 4 carbons, a haloalkoxy group having from 1 to 4 carbons, a phenyl group, a cyano group, or a nitro group; m is an integer from 0 to 5; a plurality of X moieties may be the same or different when m is 2 or greater; $G^1$ and $G^2$ each represents a protecting group that dissociates under acidic conditions, $G^1$ and $G^2$ may be the same or different, and $G^1$ and $G^2$ may bond with one another to form a ring; and

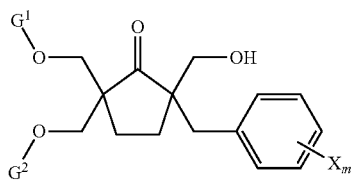
(IV)

in formula (IV), X, m, $G^1$, and $G^2$ are each the same as X, m, $G^1$, and $G^2$ in formula (V).

4. The production method for a cyclopentanone derivative according to claim 3, wherein the compound represented by formula (V) is a compound represented by formula (Va) below:

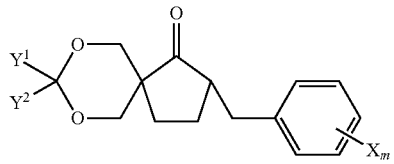
(Va)

in formula (Va), X and m are each the same as X and m in formula (V); $Y^1$ and $Y^2$ are each independently a hydrogen atom, an alkyl group having from 1 to 4 carbons, an alkenyl group having from 1 to 4 carbons, or a substituted or unsubstituted phenyl group, naphthyl group, or benzyl group; and $Y^1$ and $Y^2$ may bond with one another to form a ring.

5. The production method for a cyclopentanone derivative according to claim 4, wherein $Y^1$ and $Y^2$ are each independently a hydrogen atom or an alkyl group having from 1 to 4 carbons.

6. The production method for a cyclopentanone derivative according to claim 1, wherein both $Y^1$ and $Y^2$ are methyl groups.

7. The production method for a cyclopentanone derivative according to claim 3, wherein the compound represented by formula (V) is a compound represented by formula (Vb) below:

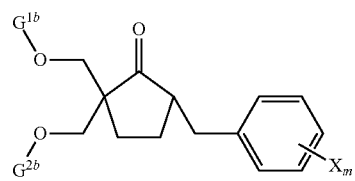
(Vb)

in formula (Vb), X and m are each the same as X and m in formula (V); and $G^{1b}$ and $G^{2b}$ are each independently an alkoxymethyl group having from 1 to 4 carbons in an alkoxy moiety, an alkoxyethyl group having from 1 to 4 carbons in an alkoxy moiety, an alkyl group having from 1 to 4 carbons, an allyl group, or a substituted or unsubstituted benzyl group, tetrahydropyranyl group, or tetrahydrofuranyl group.

8. The production method for a cyclopentanone derivative according to claim 3, wherein in formula (V), m is an integer from 0 to 3, and when m is 1 or greater, X is a halogen atom, an alkyl group having from 1 to 3 carbons, a haloalkyl group having from 1 to 3 carbons, an alkoxy group having from 1 to 3 carbons, or a haloalkoxy group having from 1 to 3 carbons.

9. The production method for a cyclopentanone derivative according to claim 3, wherein in formula (V), m is an integer from 0 to 2, and when m is 1 or 2, X is a halogen atom.

* * * * *